US007650185B2

United States Patent
Maile et al.

(10) Patent No.: US 7,650,185 B2
(45) Date of Patent: Jan. 19, 2010

(54) SYSTEM AND METHOD FOR WALKING AN IMPLANTABLE MEDICAL DEVICE FROM A SLEEP STATE

(75) Inventors: Keith R. Maile, New Brighton, MN (US); Abhijeet V. Chavan, Maple Grove, MN (US); Von Arx A. Jeffrey, Minneapolis, MN (US); Cheng Zhang, Vadnais Heights, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 597 days.

(21) Appl. No.: 11/380,112

(22) Filed: Apr. 25, 2006

(65) Prior Publication Data

US 2007/0250126 A1   Oct. 25, 2007

(51) Int. Cl.
*A61N 1/362* (2006.01)
(52) U.S. Cl. .................................... 607/16
(58) Field of Classification Search ............... 607/16
See application file for complete search history.

(56) References Cited

U.S. PATENT DOCUMENTS

| | | | |
|---|---|---|---|
| 2,786,899 A | 3/1957 | Carlisle et al. | |
| 3,536,836 A | 10/1970 | Pfeiffer | |
| 3,672,352 A | 6/1972 | Summers | |
| 3,757,770 A | 9/1973 | Brayshaw et al. | |
| 3,853,117 A | 12/1974 | Murr | |
| 3,943,915 A | 3/1976 | Severson | |
| 3,970,987 A | 7/1976 | Kolm | |
| 4,026,276 A | 5/1977 | Chubbuck | |
| 4,041,954 A | 8/1977 | Ohara | |
| 4,062,354 A | 12/1977 | Taylor et al. | |
| 4,082,097 A | 4/1978 | Mann et al. | |

(Continued)

FOREIGN PATENT DOCUMENTS

EP            0 499 939              8/1992

(Continued)

OTHER PUBLICATIONS

International Search Report and Written Opinion of international application No. PCT/US2007/067208, mailed Feb. 7, 2008, 13 pp.
Harrison et al., "A Low-Power Low-Noise CMOS Amplifier for Neural Recording Applications," IEEE Journal of Solid-State Circuits 38(6):958-965, Jun. 2003.

(Continued)

*Primary Examiner*—Carl H Layno
*Assistant Examiner*—Brian T Gedeon
(74) *Attorney, Agent, or Firm*—Faegre & Benson LLP (57) ABSTRACT

A system and method for waking up an implantable medical device ("IMD") from a sleep state in which power consumption by the IMD is essentially zero. The IMD may be adapted to perform one or more designated measurement and/or therapeutic functions. In one embodiment, the IMD includes a wake-up sensor that is adapted to sense the presence or absence of a wake-up field generated by another IMD or an external device. The wake-up field may, in some embodiments, be an electromagnetic field, a magnetic field, or a physiologically sub-threshold excitation current (i.e., E-field). Upon sensing by the wake-up sensor of the wake-up field, other components of the IMD, which may include a controller, a sensing and/or therapy module, and/or a communications module, are awakened to perform one or more designated functions.

12 Claims, 6 Drawing Sheets

U.S. PATENT DOCUMENTS

| | | | |
|---|---|---|---|
| 4,099,530 A | 7/1978 | Chen et al. |
| 4,127,110 A | 11/1978 | Bullara |
| 4,170,742 A | 10/1979 | Itagaki et al. |
| 4,206,761 A | 6/1980 | Cosman |
| 4,206,762 A | 6/1980 | Cosman |
| 4,265,252 A | 5/1981 | Chubbuck et al. |
| 4,281,666 A | 8/1981 | Cosman |
| 4,281,667 A | 8/1981 | Cosman |
| 4,340,038 A | 7/1982 | Mc Kean |
| 4,354,506 A | 10/1982 | Sakaguchi et al. |
| 4,361,153 A | 11/1982 | Slocum et al. |
| 4,378,809 A | 4/1983 | Cosman |
| 4,385,636 A | 5/1983 | Cosman |
| 4,407,296 A | 10/1983 | Anderson |
| 4,471,786 A | 9/1984 | Inagaki et al. |
| 4,481,950 A | 11/1984 | Duggan |
| 4,494,950 A | 1/1985 | Fischell |
| 4,519,401 A | 5/1985 | Ko et al. |
| 4,556,061 A | 12/1985 | Barreras et al. |
| 4,593,703 A | 6/1986 | Cosman |
| 4,596,255 A | 6/1986 | Snell et al. |
| 4,614,192 A | 9/1986 | Imran et al. |
| 4,616,640 A | 10/1986 | Kaali et al. |
| 4,651,740 A | 3/1987 | Schroeppel |
| 4,653,508 A | 3/1987 | Cosman |
| 4,660,568 A | 4/1987 | Cosman |
| 4,676,255 A | 6/1987 | Cosman |
| 4,677,985 A | 7/1987 | Bro et al. |
| 4,719,919 A | 1/1988 | Marchosky et al. |
| 4,791,936 A | 12/1988 | Snell et al. |
| 4,793,825 A | 12/1988 | Benjamin et al. |
| 4,885,002 A | 12/1989 | Watanabe et al. |
| 4,911,217 A | 3/1990 | Dunn et al. |
| 5,074,310 A | 12/1991 | Mick |
| 5,113,859 A | 5/1992 | Funke |
| 5,117,835 A | 6/1992 | Mick |
| 5,160,870 A | 11/1992 | Carson et al. |
| 5,168,869 A | 12/1992 | Chirife |
| 5,218,861 A | 6/1993 | Brown et al. |
| 5,291,899 A | 3/1994 | Watanabe et al. |
| 5,381,067 A | 1/1995 | Greenstein et al. |
| 5,423,334 A | 6/1995 | Jordan |
| 5,445,150 A | 8/1995 | Dumoulin et al. |
| 5,495,453 A | 2/1996 | Wociechowski et al. |
| 5,619,997 A | 4/1997 | Kaplan |
| 5,620,475 A | 4/1997 | Magnusson |
| 5,704,352 A | 1/1998 | Tremblay et al. |
| 5,712,917 A | 1/1998 | Offutt |
| 5,721,886 A | 2/1998 | Miller |
| 5,724,985 A | 3/1998 | Snell et al. |
| 5,743,267 A | 4/1998 | Nikolic et al. |
| 5,749,909 A | 5/1998 | Schroeppel et al. |
| 5,757,104 A | 5/1998 | Getman et al. |
| 5,759,199 A | 6/1998 | Snell et al. |
| 5,800,478 A | 9/1998 | Chen et al. |
| 5,807,258 A | 9/1998 | Cimochowski et al. |
| 5,814,089 A | 9/1998 | Stokes et al. |
| 5,833,603 A | 11/1998 | Kovacs et al. |
| 5,861,018 A | 1/1999 | Feierbach |
| 5,891,180 A | 4/1999 | Greeninger et al. |
| 5,925,001 A | 7/1999 | Hoyt et al. |
| 5,935,078 A | 8/1999 | Feierbach |
| 5,957,861 A | 9/1999 | Combs et al. |
| 5,967,989 A | 10/1999 | Cimochowski et al. |
| 6,015,387 A | 1/2000 | Schwartz et al. |
| 6,070,103 A | 5/2000 | Ogden |
| 6,140,740 A | 10/2000 | Porat et al. |
| 6,141,588 A | 10/2000 | Cox et al. |
| 6,162,238 A | 12/2000 | Kaplan et al. |
| 6,164,284 A | 12/2000 | Schulman et al. |
| 6,167,303 A | 12/2000 | Thompson |
| 6,170,488 B1 | 1/2001 | Spillman, Jr. et al. |
| 6,185,452 B1 | 2/2001 | Schulman et al. |
| 6,185,454 B1 | 2/2001 | Thompson |
| 6,185,460 B1 | 2/2001 | Thompson |
| 6,198,963 B1 | 3/2001 | Haim et al. |
| 6,198,965 B1 | 3/2001 | Penner et al. |
| 6,198,971 B1 | 3/2001 | Leysieffer |
| 6,200,265 B1 | 3/2001 | Walsh et al. |
| 6,236,889 B1 | 5/2001 | Soykan et al. |
| 6,237,398 B1 | 5/2001 | Porat et al. |
| 6,248,080 B1 | 6/2001 | Miesel et al. |
| 6,259,951 B1 | 7/2001 | Kuzma et al. |
| 6,260,152 B1 | 7/2001 | Cole et al. |
| 6,277,078 B1 | 8/2001 | Porat et al. |
| 6,315,721 B2 | 11/2001 | Schulman et al. |
| 6,432,050 B1 | 8/2002 | Porat et al. |
| 6,442,413 B1 | 8/2002 | Silver |
| 6,442,433 B1 | 8/2002 | Linberg |
| 6,472,991 B1 | 10/2002 | Schulman et al. |
| 6,473,638 B2 | 10/2002 | Ferek-Petric |
| 6,577,899 B2 | 6/2003 | Lebel et al. |
| 6,584,352 B2 | 6/2003 | Combs et al. |
| 6,607,485 B2 | 8/2003 | Bardy |
| 6,628,989 B1 | 9/2003 | Penner et al. |
| 6,644,322 B2 | 11/2003 | Webb |
| 6,664,763 B2 | 12/2003 | Echarri et al. |
| 6,671,552 B2 | 12/2003 | Merritt et al. |
| 6,712,772 B2 | 3/2004 | Cohen et al. |
| 6,731,976 B2 | 5/2004 | Penn et al. |
| 6,735,532 B2 | 5/2004 | Freed et al. |
| 6,754,538 B2 | 6/2004 | Linberg |
| 6,764,446 B2 | 7/2004 | Wolinsky et al. |
| 6,799,280 B1 | 9/2004 | Edenfield et al. |
| 6,804,557 B1 | 10/2004 | Kroll |
| 6,826,430 B2 | 11/2004 | Faltys et al. |
| 6,855,115 B2 | 2/2005 | Fonseca et al. |
| 6,873,869 B2 | 3/2005 | Fischer |
| 6,960,801 B2 | 11/2005 | Lung |
| 6,970,037 B2 | 11/2005 | Sakhuja et al. |
| 6,978,181 B1 | 12/2005 | Snell |
| 6,985,088 B2 | 1/2006 | Goetz et al. |
| 6,985,773 B2 | 1/2006 | Von Arx et al. |
| 6,988,215 B2 | 1/2006 | Splett et al. |
| 6,993,393 B2 | 1/2006 | Von Arx et al. |
| 7,003,349 B1 | 2/2006 | Andersson et al. |
| 7,013,178 B2 | 3/2006 | Reinke et al. |
| 7,024,248 B2 | 4/2006 | Penner et al. |
| 7,027,871 B2 | 4/2006 | Burnes et al. |
| 7,027,872 B2 | 4/2006 | Thompson |
| 7,060,030 B2 | 6/2006 | Von Arx et al. |
| 7,061,381 B2 | 6/2006 | Forcier et al. |
| 7,082,334 B2 | 7/2006 | Boute et al. |
| 7,123,964 B2 | 10/2006 | Betzold et al. |
| 7,212,133 B2 | 5/2007 | Goetz et al |
| 7,273,457 B2 | 9/2007 | Penner et al. |
| 7,283,874 B2 | 10/2007 | Penner et al. |
| 7,286,872 B2 | 10/2007 | Kramer et al. |
| 7,335,161 B2 | 2/2008 | Von Arx et al. |
| 7,353,063 B2 | 4/2008 | Simms, Jr. |
| 7,469,161 B1 | 12/2008 | Gandhi et al. |
| 7,479,108 B2 | 1/2009 | Rini et al. |
| 2001/0025139 A1 | 9/2001 | Pearlman |
| 2002/0151770 A1 | 10/2002 | Noll, III et al. |
| 2003/0114897 A1 | 6/2003 | Von Arx et al. |
| 2003/0114898 A1 | 6/2003 | Von Arx et al. |
| 2003/0149459 A1 | 8/2003 | Von Arx et al. |
| 2003/0158584 A1 | 8/2003 | Cates et al. |
| 2004/0039424 A1 | 2/2004 | Merritt et al. |
| 2004/0133092 A1 | 7/2004 | Kain |
| 2004/0152999 A1 | 8/2004 | Cohen et al. |
| 2004/0204744 A1 | 10/2004 | Penner et al. |
| 2004/0215279 A1 | 10/2004 | Houben et al. |
| 2005/0113705 A1 | 5/2005 | Fischell et al. |

| | | | |
|---|---|---|---|
| 2005/0159785 A1 | 7/2005 | Rueter | |
| 2005/0240245 A1 | 10/2005 | Bange et al. | |
| 2005/0288727 A1 | 12/2005 | Penner | |
| 2006/0020307 A1 | 1/2006 | Davis et al. | |
| 2006/0025834 A1 | 2/2006 | Von Arx et al. | |
| 2006/0031378 A1 | 2/2006 | Vallapureddy et al. | |
| 2006/0041287 A1 | 2/2006 | Dewing et al. | |
| 2006/0041288 A1 | 2/2006 | Dewing et al. | |
| 2006/0058627 A1 | 3/2006 | Flaherty et al. | |
| 2006/0064134 A1 | 3/2006 | Mazar et al. | |
| 2006/0064135 A1 | 3/2006 | Brockway | |
| 2006/0064142 A1 | 3/2006 | Chavan et al. | |
| 2006/0122667 A1 | 6/2006 | Chavan et al. | |
| 2006/0142819 A1 | 6/2006 | Penner et al. | |
| 2006/0149329 A1 | 7/2006 | Penner | |
| 2007/0142728 A1 | 6/2007 | Penner et al. | |
| 2007/0162090 A1 | 7/2007 | Penner | |
| 2007/0179549 A1 | 8/2007 | Russie | |
| 2008/0071178 A1 | 3/2008 | Greenland et al. | |
| 2008/0103553 A1 | 5/2008 | Penner et al. | |
| 2008/0108915 A1 | 5/2008 | Penner | |
| 2008/0171941 A1 | 7/2008 | Huelskamp et al. | |

FOREIGN PATENT DOCUMENTS

| | | |
|---|---|---|
| EP | 0 928 598 | 12/1998 |
| WO | WO98/43338 | 10/1998 |
| WO | WO99/34453 | 7/1999 |
| WO | WO00/47109 | 8/2000 |
| WO | WO01/28627 | 4/2001 |
| WO | WO01/74278 | 10/2001 |
| WO | WO01/97907 | 12/2001 |
| WO | WO02/03347 | 1/2002 |
| WO | WO03/002243 | 1/2003 |
| WO | WO03/096889 | 11/2003 |
| WO | WO2005/009535 | 2/2005 |
| WO | WO2005/053786 | 6/2005 |
| WO | WO2006/060668 | 6/2006 |
| WO | WO2007/080487 | 7/2007 |
| WO | WO2008/118908 | 10/2008 |

OTHER PUBLICATIONS

IEEE Transactions on Biomedical Engineering, vol. 42, No. 5, May 1995, Title: Data Transmission from an Implantable Biotelemeter by Load-Shift Keying Using Circuit Configuration Modulator, by Zhengnian Tang, Brian Smith, John H. Schild, and P. Hunter Peckham, pp. 524-528.

Ishiwara et al., "Current Status and Prospects of FET-Type Ferroelectric Memories," Journal of Semiconductor Technology and Science 1(1): 1-14, Mar. 2001.

Neurosurgery Clinics of North America vol. 4, No. 4, Oct. 1993, Hydrocephalus, Title: The Treatment of Hydrocephalus by Paul M. Kanev, MD, and T.S. Park, MD., pp. 611-619.

Neurosurgery Clinics of North America, vol. 4, No. 4, Oct. 1993, Hydrocephalus, Title: Complications in Ventricular Cerebrospinal Fluid Shunting by Jeffrey P. Blount, MD, John A. Campbell, MD, and Stephen J. Haines, MD, pp. 633-656.

Neurosurgery Update II Vascular, Spinal, Pediatric, and Functional Neurosurgery, Published by McGraw-Hill, Inc., 1991, Editors Robert H. Wilkins, M.D., and Setti S. Rengachary, M.D., Title Shunt Complications by R. Michael Scott, pp. 300-319.

Neurosurgery, vol. 34, No. 5, May 1994, Concepts and Innovations, Title: A New Ventricular Catheter for the Prevention and Treatment of Proximal Obstruction in Cerebrospinal Fluid Shunts, by Enrique C.G. Ventureyra, M.D., F.R.C.S.(C)., F.A.C.S., Michael J. Higgins, M.D., pp. 924-926.

Neurosurgery, vol. 34, No. 6, Jun. 1994, Rapid Communication, Title: The Use of the Codman-Medos Programmable Hakim Valve in the Management of Patients with Hydroceplhalus: Illustrative Cases, by Peter McL. Black, M.D., Ph.D., Rodolfo Hakim, M.D., Nancy Olsen Bailey, R.N., B.S.N., M.B.A., pp. 1110-1113.

Pediatric Neurosurgery 2nd Edition, Surgery of the Developing Nervous System, Published by W.B. Saunders Company Harcourt Brace Jovanovich, Inc., 1989. Title: Treatment of Hydrocephalus by Harold L. Rekate, M.D.; Ventricular Shunts: Complications and Results by Robert L. McLaurin, M.D.; pp. 200-229.

Fig. 9 ary implantable medi-

SYSTEM AND METHOD FOR WALKING AN IMPLANTABLE MEDICAL DEVICE FROM A SLEEP STATE

TECHNICAL FIELD

The present invention generally relates to implantable medical devices and/or sensors. More particularly, embodiments of the present invention relate to systems and methods for waking up implantable medical devices from powered off or low power states.

BACKGROUND

Implantable medical devices ("IMDs") configured to be implanted in a human body and to perform one or more therapeutic functions, such as drug delivery, cardiac pacing, cardiac defibrillation, neural stimulation, and the like, are known. Additionally, IMDs are known that can be implanted within a patient's body for measuring one or more physiologic parameters. For example, sensors or transducers can be implanted in the body for monitoring a variety of properties, such as temperature, blood pressure, strain, fluid flow, chemical properties, electrical properties, magnetic properties, and the like. Such IMDs can be placed at various locations throughout a person's body, thereby providing a heterogeneous mix of physiologic data. The IMDs making up such systems typically include components adapted for bi-directional wireless communication, allowing the IMDs to transmit data to and receive data from other IMDs and/or devices external to the patient.

The foregoing types of IMDs used for sensing physiological parameters are typically size and space constrained, which in turn, constrains the size and capacity of the power supply (e.g., battery) for providing power to the various IMD components and circuitry. Accordingly, such IMDs must be maintained in a low power or powered off state for the majority of the time, and are ideally energized only to perform their designated functions, after which time they must be returned to their powered down state.

Thus, a need exists for systems and methods for activating IMDs from a low power or powered off state that require minimal power and physical space within the IMD housing.

SUMMARY

The present invention, in one embodiment, is a method carried out by a satellite implantable medical device for being awakened from a sleep state by a primary implantable medical device. The satellite implantable medical device includes a wake-up sensor, a control module, a physiologic sensor, and a communication module. The method comprises waiting in a sleep state, and then detecting, by the wake-up sensor, the presence of a wake-up field generated by the primary implantable medical device. Then, responsive to the presence of the wake-up field, the method includes causing the control module to change from the sleep state to an active state and to cause the communications module to transmit a measurement of at least one physiologic parameter to the primary implantable medical device. The physiologic parameter is measured by the physiologic sensor.

The present invention, in another embodiment, is a method of waking an implantable medical device from a low-power state. The method comprises providing a first implanted medical device including a wake-up field generator and a first communication module, and also providing a second implanted medical device including a battery, a wake-up sensor operable to detect the wake-up field, a physiologic sensor, a control module, and a second communication module, with the second implanted device initially in a low-power state. The method then includes detecting a presence of the wake-up field. Then, the method includes, responsive to the presence of the wake-up field, causing the control module to change from the low-power state to an active state and to cause a measurement of at least one physiological parameter to be transmitted to the first implanted device via the second communication module.

The present invention, in yet another embodiment, is a system for waking up an implantable medical device from a sleep state. The system comprises a primary implantable device including a wake-up field generator operable to generate a wake-up field, and a first communication module. The system further comprises a satellite implantable device including a control module and a second communication module, wherein the control module and the second communication module are adapted to change between a sleep state and an active state. The satellite implantable device further includes means for detecting the wake-up field and causing the control module to change from the sleep state to the active state.

While multiple embodiments are disclosed, still other embodiments of the present invention will become apparent to those skilled in the art from the following detailed description, which shows and describes illustrative embodiments of the invention. Accordingly, the drawings and detailed description are to be regarded as illustrative in nature and not restrictive.

While the invention is amenable to various modifications and alternative forms, specific embodiments have been shown by way of example in the drawings and are described in detail below. The intention, however, is not to limit the invention to the particular embodiments described. On the contrary, the invention is intended to cover all modifications, equivalents, and alternatives falling within the scope of the invention as defined by the appended claims.

DETAILED DESCRIPTION

Figure 1:
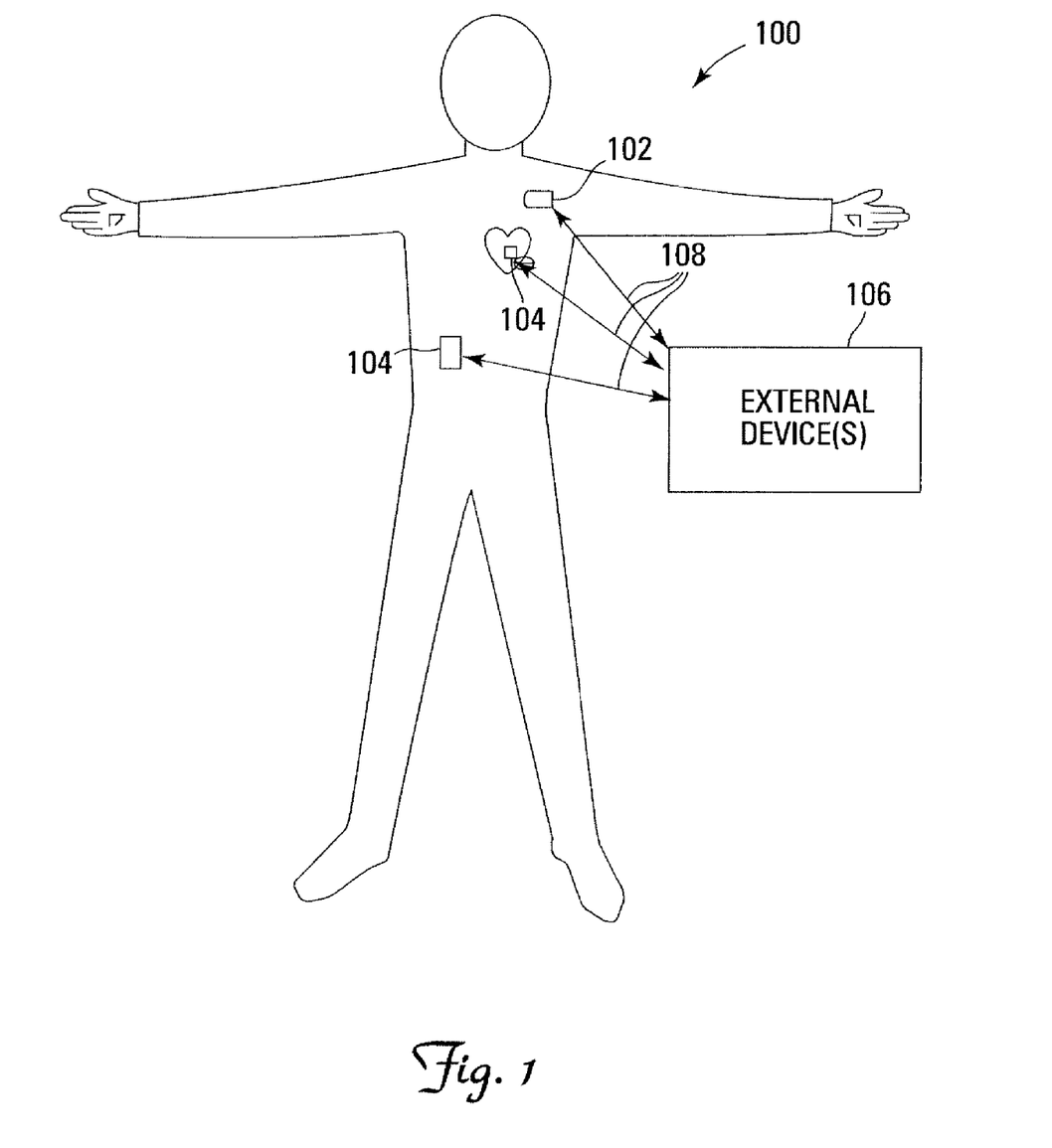
FIG. 1 is a simplified depiction of a human body in which a system or network of implantable medical devices is implanted according to one embodiment of the present invention.

FIG. 1 illustrates a simplified human body in which a system or network 100 of implantable medical devices is implanted. As shown in FIG. 1, the system 100 includes a primary IMD 102 and at least one satellite IMD 104. Although the primary and satellite IMDs 102, 104 are shown implanted in specific locations, in practice, either or both of the primary and satellite IMDs 102, 104 may be implanted anywhere in the body. The system 100 may also include an external device 106 (e.g., a computing device and/or programming device), which may communicate with the primary or satellite IMDs 102, 104 via communication channels 108. Although FIG. 1 illustrates a system 100 utilizing two satellite IMDs 104, those skilled in the art will appreciate that one or more than two satellite IMDs 104 may be used within the scope of the present invention.

The satellite IMD 104 may be configured to perform one or more designated functions, which may include taking one or more physiological measurements and/or delivering a desired therapy. The implantation sites for the satellite IMDs 104 are determined based on the particular therapeutic needs of the patient. In one embodiment, the satellite IMD 104 is adapted to be implanted and to measure blood pressure within the patient's pulmonary artery, and to store and/or transmit blood pressure data to the primary IMD 102, another IMD, or the external device(s) 106. In another embodiment, the satellite IMD 104 is adapted to deliver a desired therapy (e.g., a pacing and/or defibrillation stimulus) to the patient's heart or cardiovascular system.

The satellite IMD 104 includes power supply components (e.g., a battery) for providing electrical power to the various components and/or circuitry for performing the functions described above. The satellite IMD 104 is desirably made as small as possible, however, which constrains the space within the IMD 104 that is available for power supply components. Such space constraints limit the capacity of these power supply components. In an effort to maximize the longevity of the satellite IMD 104, its power consumption is minimized, and thus, the average power consumption of the satellite IMD 104 is desirably very low. For example, in one embodiment, size constraints may limit the satellite IMD 104 to a 1000 microamp-hour, non-rechargeable battery. In such a case, the average power consumption of the satellite IMD 104 must be less than 10.0 nA to provide a 10 year longevity. In other embodiments, the average power consumption goals may be even lower where, for example, the battery is significantly smaller and/or a greater longevity is desired.

In order to achieve this low power consumption, the satellite IMD 104 is normally in a "sleep" or "sleeping" state characterized by a power consumption of from essentially zero (i.e., a completely powered off state) to a low power state in which only a minimal circuitry (e.g., a timer or comparator) are energized and consuming electrical power. The satellite IMD 104, or specific aspects thereof, is awakened (i.e., powered on) to an active state in which it can perform one or more designated functions. The terms "wake," "waking," "wake-up," and "awaken(ed)" relate to the operation of powering on or energizing one or more aspects of the satellite IMD 104 to an active state, such that the awakened portion can perform a designated function.

The satellite IMD 104 may be awakened by, for example, the primary IMD 102 or the external device 106. As discussed in detail below in connection with the various exemplary embodiments of the present invention, circuitry within the satellite IMD 104 is adapted to detect a wake-up field generated by the primary IMD 102 or external device 106, and to cause the satellite IMD 104 to awake and perform its designated functions. The satellite IMD 104 is desirably in the active state only to the extent necessary to perform its designated diagnostic and/or therapeutic function(s), after which time it returns to its sleep state. Additionally, in some embodiments, to maximize satellite IMD 104 longevity, the power consumption of the various circuitry for waking up the satellite IMD 104 is desirably less than about 10 percent of the total power consumption of the satellite IMD 104.

The primary IMD 102 operates, in one embodiment, to wake the satellite IMD 104 from the sleep state, and may further be configured to direct the satellite IMD 104 to perform one or more designated functions. The primary IMD 102 itself may also be configured to perform therapeutic functions or to take physiologic measurements. For example, the primary IMD 102 may, in one embodiment, be a pulse generator for providing a cardiac pacing and/or defibrillation stimulus. The therapeutic functions are not limited to any particular type and can include, for example, drug delivery therapy, or any other therapy capable of being administered with an IMD currently known or later developed. Additionally, the primary IMD 102 may be configured to measure physiologic parameters such as blood pressure, temperature, blood or fluid flow, strain, electrical, chemical, or magnetic properties within the body.

It is emphasized, however, that neither the satellite IMD 104 nor the primary IMD 102 are limited to any particular type or types of devices. To the contrary, the satellite IMD 104 can be any IMD that is normally in a sleep state to minimize power consumption and is awakened only as necessary to perform a desired function. Similarly, the primary IMD 102 can be any IMD that operates, at least in part, to cause a satellite IMD 104 to wake from a sleep state. Thus, in this regard, the satellite IMD 104 may sometimes also function as a primary IMD 102 in a given embodiment. That is, the satellite IMD 104 may be configured such that, in its active state, it can cause another satellite IMD 104 to wake and perform one or more desired functions.

Figure 2:
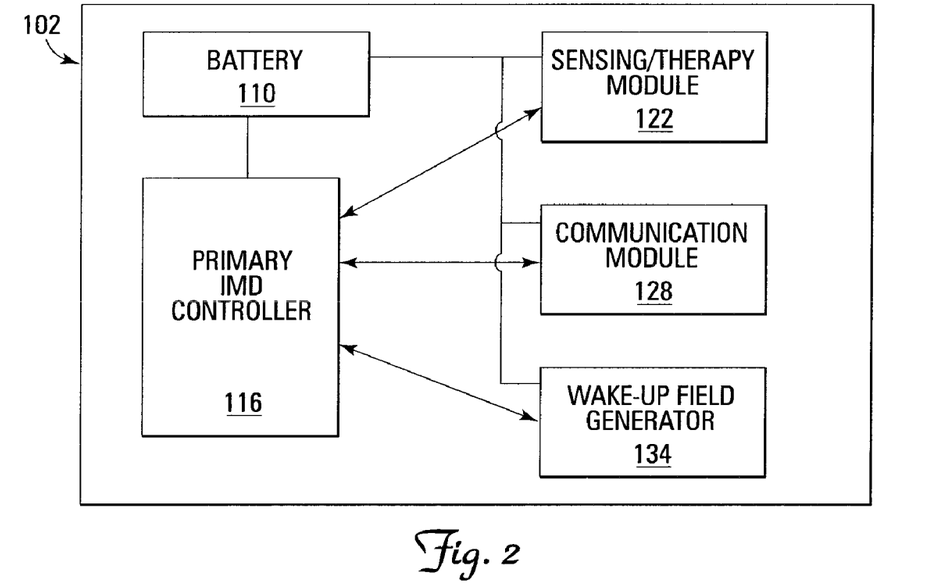
FIG. 2 is a functional block diagram illustrating a primary implantable medical device according to one embodiment of the present invention.

FIG. 2 is a functional block diagram illustrating one embodiment of the primary IMD 102. As shown in FIG. 2, the primary IMD 102 includes, in one embodiment, a battery 110, a primary IMD controller 116, a sensing and/or therapy module 122, a communication module 128, and a wake-up field generator 134. In some embodiments, the primary IMD 102 may not include the sensing and/or therapy module 208. The term "module" is not intended to imply any particular structure. Rather, "module" may mean components and circuitry integrated into a single unit as well as individual, discrete components and circuitry that are functionally related.

The battery 110 operates to provide operating power to the controller 116, the sensing and/or therapy module 122, the communication module 128, and the wake-up field generator 134. The controller 116 operates to control the sensing and/or therapy module 122, the communication module 128, and the wake-up field generator 134, all of which are operatively coupled to and communicate with the controller 116. For example, the controller 116 may command the sensing and/or therapy module 122 to deliver a desired therapy, such as a pacing or defibrillation stimulus. Additionally, the controller 116 may command the communication module 128 to transmit and/or receive data from the external device 106 or the satellite IMDs 104. Still additionally, the controller 116 may command the wake-up field generator 134 to generate a field (e.g., electromagnetic, magnetic, E-field) that can be detected by a sensor in the satellite IMD 104, as discussed in detail below.

The controller 116 may include a microprocessor or microcontroller coupled to a memory device that includes operating instructions and/or software for the microprocessor or microcontroller. Additionally, or alternatively, primary IMD may include timing circuitry which operates to schedule, prompt, and/or activate the primary IMD 102 to perform various activities. For example, in one embodiment, the timing circuitry may be utilized to determine the appropriate time at which one or more satellite IMDs 104 should wake in order to perform a designated function. In one embodiment, the timing circuitry may be an internal timer or oscillator, while in other embodiments, timing may be performed by specific hardware components that contain hardwired logic for performing the steps, or by any combination of programmed computer components and custom hardware components.

As those skilled in the art will appreciate, processors, memory devices, and timing devices are well known, and the specific type and/or style of such devices that can be used in the primary IMD 102 is not limited. To the contrary, any suitable processing, memory, and timing device, or devices, currently known or later developed, may be used.

The communication module 128 is configured to allow the primary IMD 102 to communicate with other devices, such as the external device 106 or a satellite IMD 104. In one embodiment, the primary IMD 102 may communicate with other devices via a wireless connection. Various types of wireless communication circuitry are well known in the art, and the specific type and/or style of wireless communication that can be used is not limited. For example, ultrasonic waves, acoustic communications, radio frequency communications, and the like may be used. In one embodiment, the communication module 128 includes an acoustic transmitter/receiver configured for acoustic telemetry.

The sensing and/or therapy module 122, if present, operates to perform the therapeutic and/or diagnostic functions described above. Thus, in one embodiment, the sensing and/or therapy module 122 may deliver a cardiac pacing and/or defibrillation stimulus. Again, the sensing and/or therapy module 122 is not limited to performing any particular type of physiologic measurement or therapy.

The wake-up field generator 134 operates to generate a field (i.e., a wake-up field) that can be detected by a sensing module in the satellite IMD 104 for the purpose of causing the satellite IMD 104 to wake from the sleep state. As will be discussed in detail below, various types of wake-up fields (e.g., electromagnetic, magnetic, electric) are contemplated within the scope of the present invention. The particular type of wake-up field utilized will depend on variables such as the available power supply and the implantation site(s) of the primary and satellite IMDs 102, 104, and their proximity to one another.

Figure 3:
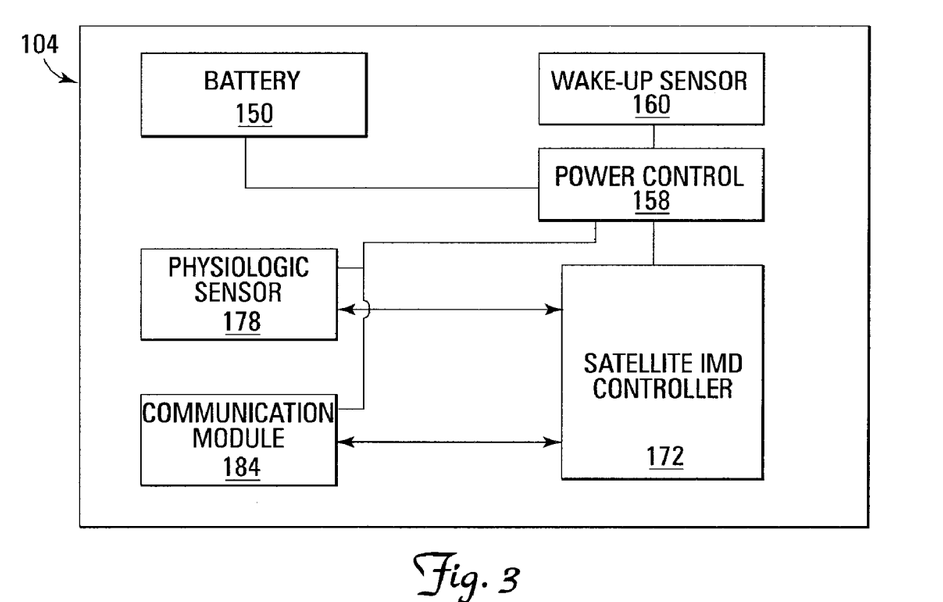
FIG. 3 is a functional block diagram illustrating a satellite implantable medical device according to one embodiment of the present invention.

FIG. 3 is a functional block diagram illustrating one embodiment of a satellite IMD 104. As shown in FIG. 3, the satellite IMD 104 includes a battery 150, power control circuitry 158, a wake-up sensor 160, a satellite IMD controller 172, a physiologic sensor 178, and a communication module 184. In one embodiment, the battery 150 may be rechargeable. The battery 150 operates to supply power to the wake-up sensor 160, the controller 172, the physiologic sensor 178, and the communication module 184. The power control circuitry 158 is operatively connected to the battery 150 and the wake-up sensor 160, and operates to regulate the supply of power from the battery 150 to the wake-up sensor 160, the controller 172, the physiologic sensor 178, and the communication module 184.

The controller 172 may be of substantially the same type as or identical to the controller 116 of the primary IMD 102, and may include a microprocessor or microcontroller coupled to a memory device that includes operating instructions and/or software for the microprocessor or microcontroller. Additionally, or alternatively, the satellite IMD 102, and in particular the controller 172, may include timing circuitry which operates to direct the activities of the satellite IMD 104 (e.g., taking and storing physiologic measurements, uploading measurement data) after it has been awakened from its sleep state. Alternatively, the satellite IMD controller 172 may have reduced functionality as compared to the primary IMD controller 116, in embodiments where the functional requirements of the satellite IMD 172 are less extensive.

The physiologic sensor 178 performs functions related to measurement of physiologic parameters, and is not limited to any particular type of physiologic measurement. For example, the physiologic sensor 178 may be a pressure sensor adapted to measure internal pressure in a blood vessel. In one such embodiment, the satellite IMD 104 is implanted in the patient's pulmonary artery, and the physiologic sensor 178 is adapted to measure blood pressure therein. In some embodiments, the satellite IMD 104 may have the capability to perform one or more therapeutic functions (e.g., cardiac pacing, drug delivery) in addition to, or in lieu of, one or more measurement functions. In one such embodiment, the satellite IMD 104 includes a therapy delivery module and does not include the physiologic sensor 178.

The communication module 184 operates to allow the satellite IMD 104 to communicate with other devices, such as the external device 106, the primary IMD 102, or other satellite IMDs 104. As discussed above, the satellite IMD 104 can communicate with other devices via a wireless connection. As with the primary IMD 102, the specific type and/or style of wireless communication that can be used is not limited. For example, ultrasonic waves, acoustic communications, radio frequency communications, and the like may be used by the communication circuitry. In one embodiment, the communication module 184 is an acoustic telemetry module and includes an acoustic transmitter/receiver adapted to transmit and receive acoustic signals to/from the primary IMD communication module 128. In one such embodiment, the transmitter/receiver includes an ultrasonic transducer and associated circuitry.

In some embodiments, the controller 172, physiologic sensor 178, and the communication module 184 may be integrated into an integrated circuit, while in other embodiments one or more of these elements may be discrete hardware and circuitry.

The wake-up sensor 160 includes one or more sensors and circuitry adapted to detect and/or to react to the presence of a wake-up field generated by the wake-up field generator 134 of the primary IMD 102. The wake-up sensor 160 is further adapted to cause, upon detecting the presence of such a wake-up field, the controller 172, the physiologic sensor 178, and/or the communication module 184 to be awakened, via the power control circuitry 158, as appropriate for performing one or more designated functions such as those described above. In one embodiment, the satellite IMD 104 is configured such that, upon the wake-up sensor 160 detecting a wake-up field, the controller 172 is initially awakened. Thereafter, the controller 172 directs the subsequent wake-up and operation of the other functional portions (e.g., the communication module 184 and/or the physiologic sensor 178).

As discussed in detail below, in some embodiments, the wake-up sensor 160 consumes minimal power while the satellite IMD 104 is in the sleep state, with only a minimal amount of circuitry (e.g., a comparator) powered on for detecting and processing the output (i.e., an output voltage), if any, from the sensing circuitry of the wake-up sensor 160. In other embodiments the wake-up sensor 160 may be of a type (e.g., a Hall effect sensor) having power requirements significant enough to require duty cycling of the wake-up sensor 160 in order to achieve the aforementioned average power consumption and longevity goals.

In some embodiments, the wake-up field may be modulated such that the satellite IMD 104 can identify the field as a wake-up field from the primary IMD 102. This may be particularly advantageous in a system 100 utilizing multiple primary and satellite IMDs 102 and 104.

Figure 4:
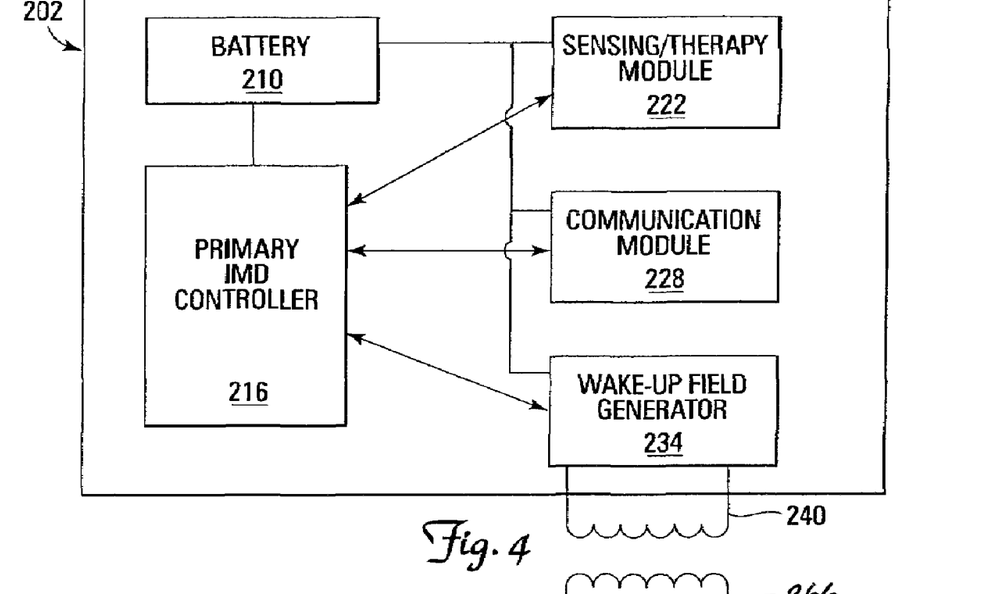
FIGS. 4 and 5 are functional block diagrams illustrating primary and satellite implantable medical devices utilizing inductive coupling to wake the satellite implantable medical device from a sleep state, according to one embodiment of the present invention.
Figure 5:
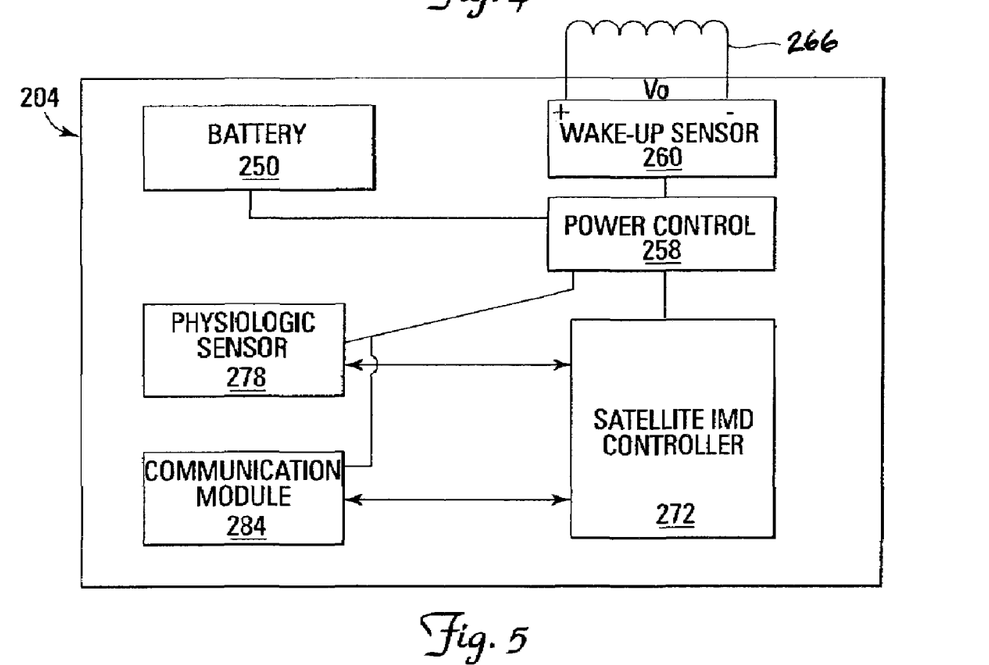

FIGS. 4 and 5 are functional block diagrams of a primary IMD 202 and a satellite IMD 204, respectively, according to one exemplary embodiment of the present invention utilizing inductive coupling of the IMDs 202 and 204 to wake the satellite IMD 204. Accordingly, as shown in FIG. 4, the primary IMD 202 includes a battery 210, a primary IMD controller 216, a sensing and/or therapy module 222, a communication module 228, and a wake-up field generator 234, which in the illustrated embodiment includes an inductive coil 240. As shown in FIG. 5, the satellite IMD 204 includes a battery 250, power control circuitry 258, a wake-up sensor 260 which in the illustrated embodiment includes an inductive coil 266, a satellite IMD controller 272, a physiologic sensor 278, and a communication module 284. In general, the batteries 210, 250, the controllers 216, 272, the sensing and/or therapy module 222, the physiologic sensor 278, and the communication modules 228 and 284 are configured and operate as described above with respect to the corresponding elements of the IMDs 102 and 104.

In the illustrated embodiment of FIGS. 4 and 5, the inductive coils 240 and 266 are inductively coupled. As those skilled in the art will appreciate, with the coils 240, 266 inductively coupled, passing an alternating current through the inductive coil 240 generates an electromagnetic field, which in turn generates an A/C output voltage $V_o$ across the inductive coil 266. Circuitry within the wake-up sensor, 260 (e.g., a comparator), detects this output voltage, which is then amplified to trigger, via the power control circuitry 258, the wake-up of at least the satellite IMD controller 272, and as appropriate, the physiologic sensor 278, and/or the communication module 284.

Additionally, in some embodiments in which inductive telemetry is used as the primary communications means between the primary and satellite IMDs 202 and 204 (i.e., via the communications modules 228 and 284), the same inductive coils 240, 266 may also advantageously be used for communications/telemetry, thereby reducing the overall number of components required.

In another embodiment, the wake-up field generator 234 may generate a magnetic wake-up field, and the wake-up field sensor 260 may include a passive magnetic field sensing device such as a reed switch. In such an embodiment, the IMDs 202 and 204 need not be inductively coupled via the inductive coils 240 and 266.

Figure 6:
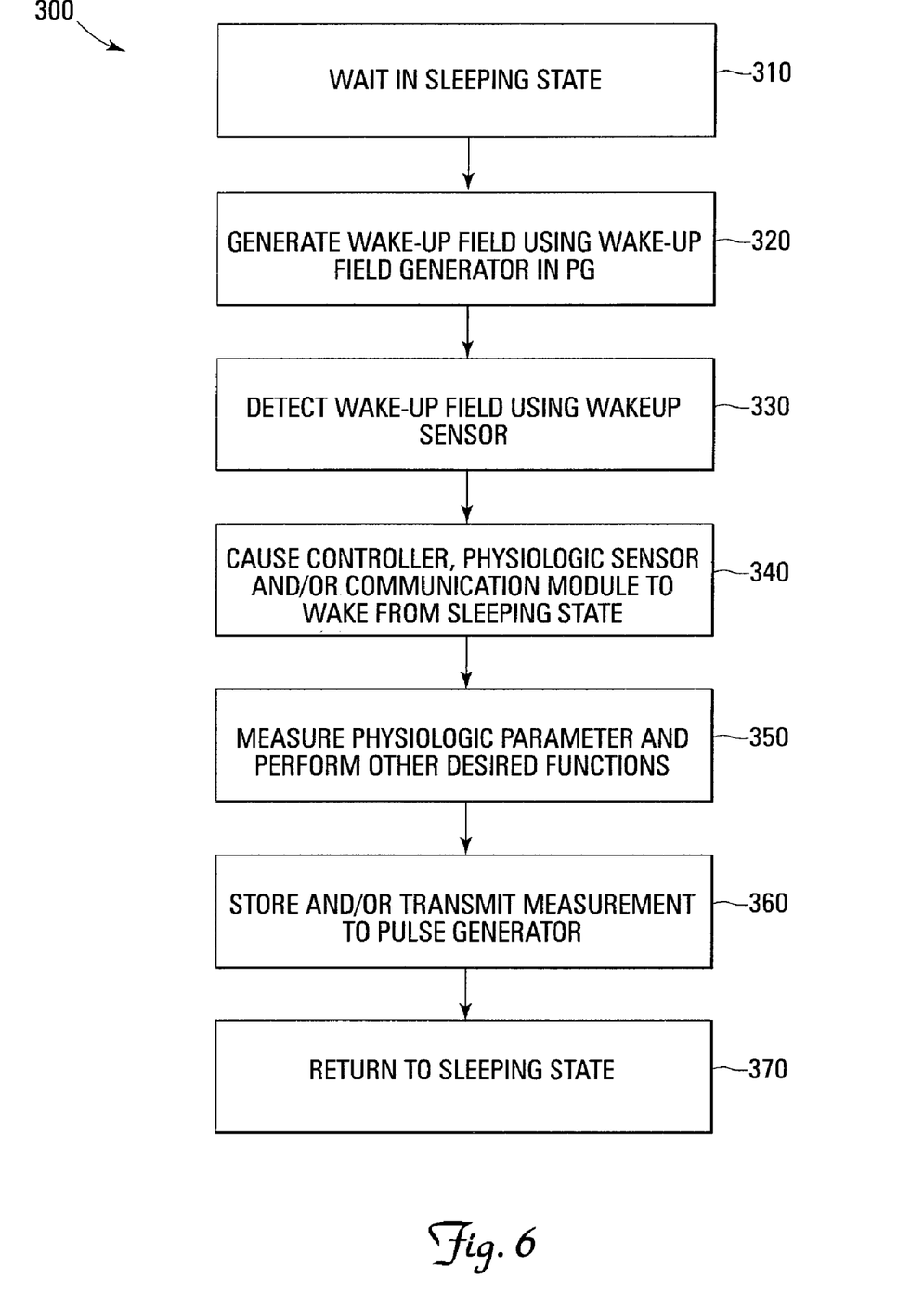
FIG. 6 is a flow chart illustrating an exemplary algorithm for waking up a satellite implantable device according to one embodiment of the present invention.

FIG. 6 is a flow chart illustrating an exemplary algorithm 300 for waking up a sleeping satellite IMD, such as the satellite IMD 204 of FIG. 5, for the performance of one or more designated functions. In this particular embodiment, it is assumed that the physiologic sensor 278 performs the designated measurement function of measuring blood pressure in the pulmonary artery, which measurement may then be transmitted to the primary IMD 202 via the communication module 284. Wake-up of the satellite IMD 202 is coordinated by the primary IMD 202, which may trigger the satellite IMD 204 to wake-up at a scheduled time, in response to a specified event, or a command from another IMD or an external device.

In this particular embodiment, for illustrative purposes, it is assumed that the primary IMD 202 is a pulse generator ("PG") adapted to provide a cardiac pacing and/or defibrillation stimulus. In this embodiment, the satellite IMD controller 272 may facilitate coordination of data communications and performance of designated functions by the satellite IMD 204.

As stated above, in order to conserve energy, the satellite IMD 204 will generally be in the sleeping state, effectively performing a waiting operation 310 and consuming a minimal amount of power. When appropriate (as determined by a specified event, time interval, command from an external device, etc.) the primary IMD 204, and specifically, the wake-up field generator 234, will generate a wake-up field. In the embodiment illustrated in FIGS. 4 and 5, this wake-up field is in the form of an electromagnetic field generated by the inductive coil 240.

The wake-up sensor 260 detects, or reacts to, the wake-up field (block 330). Thus, in the embodiment illustrated in FIGS. 4 and 5, the electromagnetic wake-up field generated by the inductive coil 240 produces an output voltage across the inductive coil 266, which in turn causes the satellite IMD controller 272, physiologic sensor 278, and/or the communication module 284 to be energized and thereby awakened from the sleeping state (block 340). The physiologic sensor 278 then measures the desired physiologic parameter, in this case, the pulmonary arterial blood pressure, and if appropriate, performs other desired functions (block 350). The blood pressure measurement may then be stored in memory and/or may be transmitted to the primary IMD 202 or an external device via the communication module 284 (block 360). Upon completion of all of its desired functions, the satellite IMD 204 returns to its sleeping state.

Figure 7:
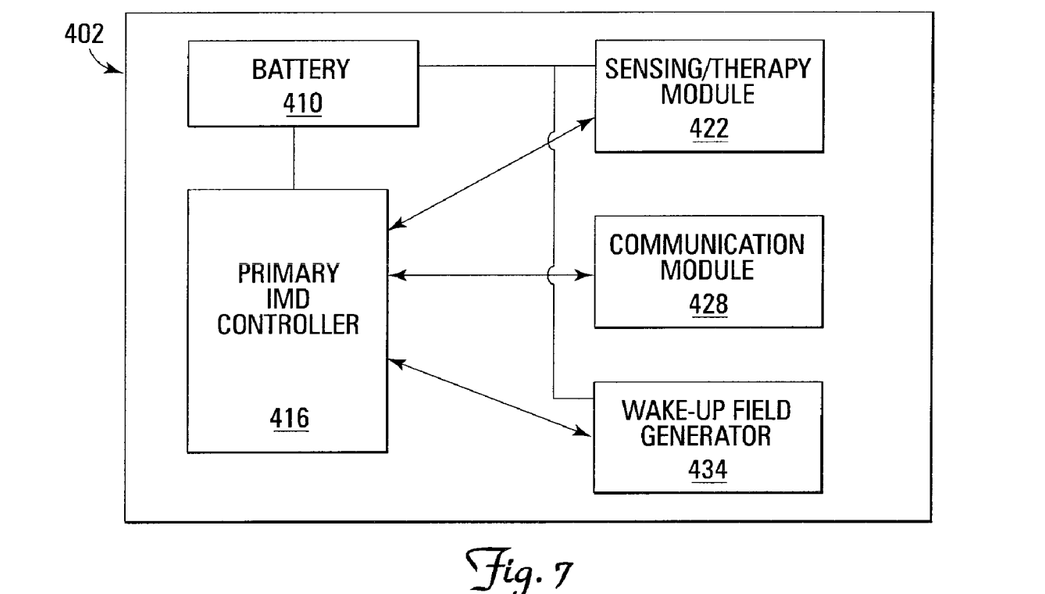
FIGS. 7 and 8 are functional block diagrams illustrating primary and satellite implantable medical devices according to additional embodiments of the present invention.
Figure 8:
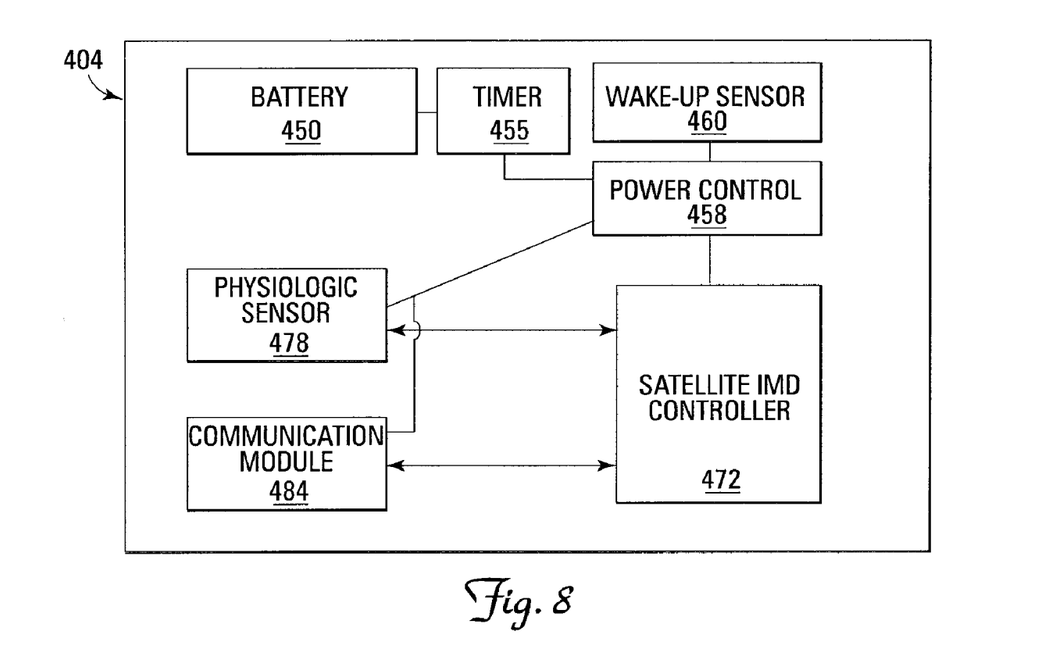

FIGS. 7 and 8 are functional block diagrams of a primary IMD 402 and a satellite IMD 404, respectively, according to another exemplary embodiment of the present invention. As shown in FIG. 7, the primary IMD 402 includes a battery 410, a primary IMD controller 416, a sensing and/or therapy module 422, a communication module 428, and a wake-up field generator 434. As shown in FIG. 8, the satellite IMD 404 includes a battery 450, a wake-up timer 455, power control circuitry 458, a wake-up sensor 460, a satellite IMD controller 472, a physiologic sensor 478, and a communication module 484. In general, the batteries 410, 450, the controllers 416, 472, the sensing and/or therapy module 422, the physiologic sensor 478, and the communication modules 428 and 484 are configured and operate as described above with respect to the corresponding elements of the IMDs 102, 202, and 104, 204. Additionally, the wake-up sensor 460, the satellite IMD controller 472, the physiologic sensor 478, and the communication module 484 are normally in the sleeping state, consuming essentially no power from the battery 450.

In the embodiment shown in FIGS. 7 and 8, the wake-up sensor 460 is of a type having power requirements significant enough to require the wake-up sensor 460 to be duty cycled in order to achieve the power consumption and longevity goals discussed above. In exemplary embodiments, such wake-up sensors 460 may include magnetic field sensors such as Hall Effect sensors, and electric field ("E-field") sensors. Accordingly, in one embodiment, to conserve power, the wake-up sensor 460 is normally in a sleep state, and is energized at scheduled sampling intervals to search for and detect a wake-up field generated by the wake-up field generator 434. The frequency and duration of the sampling intervals are predetermined based on variables including, without limitation, the power requirements of the wake-up sensor 460, the battery volume, and the desired longevity of the satellite IMD 404. In another embodiment, the wake-up sensor 460 is always powered on and is not duty cycled.

In the duty cycled embodiments, the wake-up timer 455 and the power control circuitry 458 are operatively connected to the battery 450 and operate to regulate the power supply to the wake-up sensor 460. Additionally, as with the embodiments described above with respect to FIGS. 3 and 5, the power control circuitry 458 operates to regulate the supply of power to the satellite IMD controller 472, the physiologic sensor 478, and the communication module 484. The wake-up timer 455 is a low power device, e.g., an oscillator, having power consumption characteristics selected based on variables such as the battery volume and the desired longevity. The timer 455 operates to cause, via the power control circuitry 458, the wake-up sensor 460 to be energized (i.e., to awaken from the sleep state) such that it can sense a wake-up field generated by the wake-up field generator 434. The wake-up timer 455 is further adapted to cause the wake-up sensor 460 to return to its sleep state after a predetermined time interval if no such wake-up field is present.

In one embodiment, the wake-up sensor 460 may be a low duty cycle Hall Effect sensor adapted to sense a magnetic field generated by the wake-up field generator 434. The principles of operation of Hall Effect sensors are known in the art, and so a detailed description of such principles is not required. In this embodiment, the wake-up field generator 434 is adapted to generate a magnetic wake-up field, which can propagate through the patient's body tissue to reach the Hall Effect sensor 460. The Hall Effect sensor 460 is adapted to sense the propagated magnetic wake-up field and to produce an output voltage that in turn causes the satellite IMD controller 472, and the physiologic sensor 478 and/or the communication module 484 to be awakened as appropriate.

In another embodiment, the wake-up field generator 434 is an E-field generator adapted to generate and transmit a physiologically sub-threshold excitation current that can propagate through the patient's body tissue to the wake-up sensor 460. In this embodiment, the wake-up sensor 460 is adapted to sense the excitation current and generate an output voltage that causes the satellite IMD controller 472, the physiologic sensor 478, and/or the communication module 484 to be awakened.

It should be noted that the foregoing exemplary types of wake-up field generators and wake-up sensors 434 and 460 are not exclusive. For example, in another embodiment, the wake-up field generator 434 may include an LED source operating at a tissue-penetrating wavelength, and the wake-up sensor 460 may include a duty-cycled photo diode. In yet another embodiment, the wake-up sensor 460 may be a low power, low duty cycle accelerometer, and the wake-up field generator 434 is provided in an external device (i.e., not in the primary IMD 402), and is adapted to mechanically vibrate the wake-up sensor 460 at the appropriate time(s).

Figure 9:
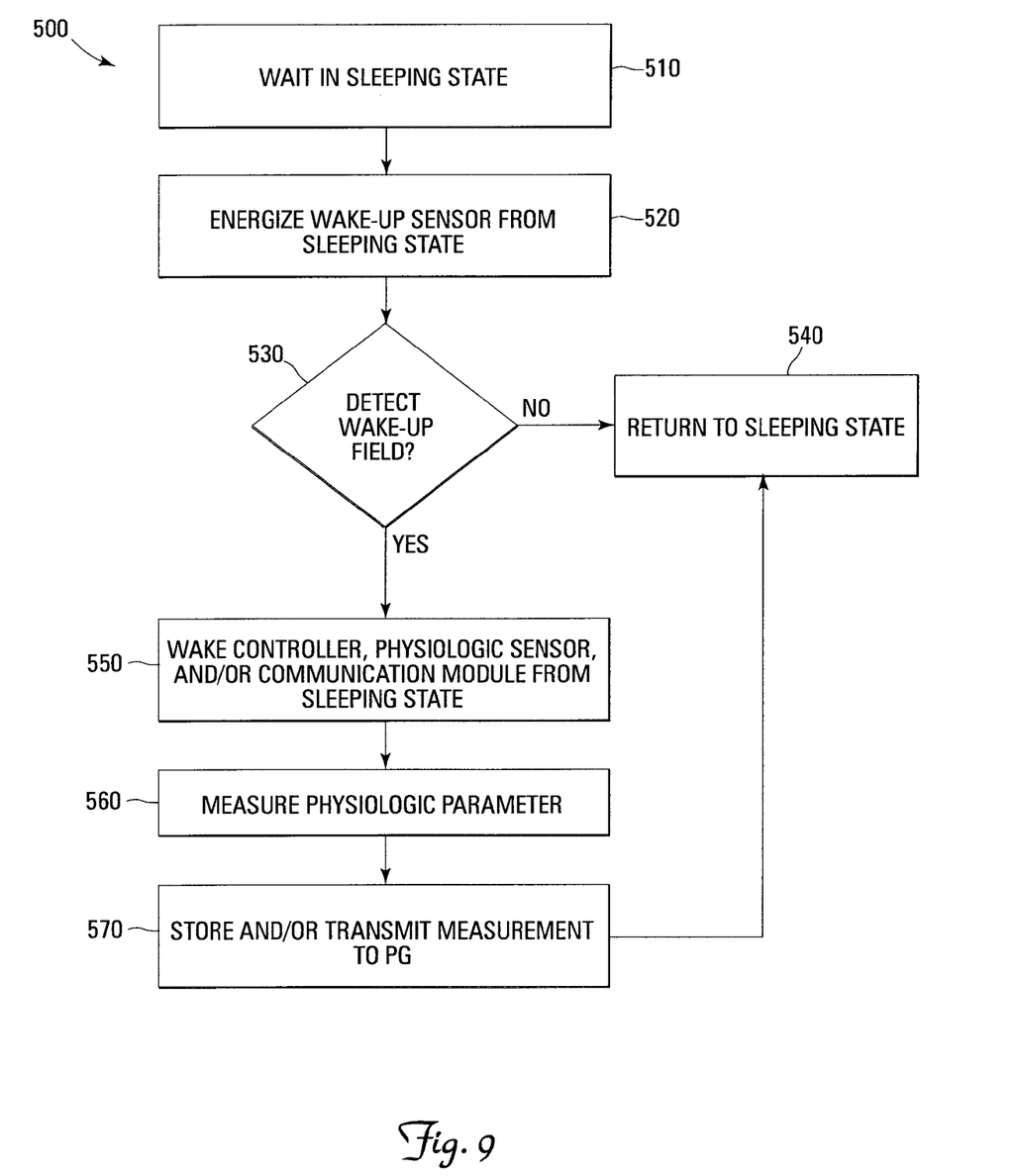
FIG. 9 is a flow chart illustrating an exemplary algorithm for waking up a satellite implantable device according to another embodiment of the present invention.

FIG. 9 is a flow chart illustrating an exemplary algorithm 500 for waking the satellite IMD 404. For illustration purposes, it is assumed that the primary IMD 402 is a pulse generator (PG), and the physiologic sensor 478 of the satellite IMD 404 is adapted to measure blood pressure in the pulmonary artery. The primary IMD 402 may trigger the measurement at a scheduled time, in response to a specified event, or a command from another IMD or an external device.

As shown in FIG. 9, the satellite IMD 404 initially performs a waiting operation in which the satellite IMD 404 is in a sleeping state (block 510). In this state, in the embodiment illustrated in FIG. 8, the wake-up timer 455 is powered on and operating, and the wake-up sensor 460 is powered off. The waiting operation 402 waits for a scheduled time. Upon the occurrence of the predetermined scheduled time, the wake-up timer 455 causes, via the power control circuitry 458, the wake-up sensor 460 to be energized such that it can detect the presence of a wake-up field generated by the wake-up field generator 434 of the primary IMD 402 (blocks 520-530).

If the wake-up sensor 460 does not detect a wake-up field during a specified time period as measured by the wake-up timer 455, the wake-up sensor 460 is returned to its sleep state (block 540). If, however, the wake-up sensor 460 detects a wake-up field, it then causes the controller 472, and as appropriate or necessary, the physiologic sensor 478 and/or the communication module 484, to be awakened (block 550), via the power control circuitry 458, to perform their designated functions. In the illustrated embodiment, the physiologic sensor 478 then measures the desired physiologic parameter, in this case, blood pressure in the pulmonary artery, and if appropriate, performs other desired functions (block 560). The blood pressure measurement may then be stored in memory and/or may be transmitted to the primary IMD 402 or an external device via the communication module 484 (block 570). Upon completion of all of its desired functions, the satellite IMD 404 returns to its sleeping state (block 540).

Thus, in the illustrated embodiment, only the wake-up timer 455 and a minimal amount of circuitry (e.g., a comparator in the wake-up sensor 460) is energized while in the sleep state. Moreover, the wake-up sensor 460 and wake-up timer 455 of the illustrated embodiment have substantially lower power requirements than prior wake-up methodologies using the primary communication/telemetry circuitry for wake-up purposes.

In the embodiments illustrated in FIGS. 7-9, because the sensing of the wake-up field by the wake-up sensor 460 is a timed event, it may be advantageous to coordinate the timing of the generation of the wake-up field by the wake-up field generator 434 with the timing of the energization (i.e., awakening) of the wake-up sensor 460. In this way, the overall awake time of the wake-up sensor 460 can be reduced, thereby conserving power, without detrimentally affecting the ability of the wake-up sensor 460 to sense all wake-up events triggered by the primary IMD 402. Such coordination can be accomplished, for example, via the systems and methods disclosed in co-pending U.S. patent application Ser. No. 11/186,245 entitled "Systems and Methods for Timing-Based Communication Between Implantable Medical Devices," which is incorporated herein by reference in its entirety for all purposes.

It is emphasized that any of the wake-up fields described above may be generated by a wake-up generator in the external device(s) 106. That is, the present invention is not limited to wake-up operations triggered by an implantable medical device.

In addition, in some embodiments, the satellite IMD 104, 204, 304, or 404 is not fully awakened in all situations. Rather, the satellite IMD may be configured such that, upon sensing the wake-up field, individual components are awakened in stages. For example, the satellite IMD controller 172, 272, 373, or 472 may initially be the only component that is awakened, and it may thereafter direct other components to be awakened only as necessary based on its operating instructions. Alternatively, in other embodiments, only the communication modules 184, 284, 384 or 484 may be initially awakened, and the subsequent actions of the satellite IMD may be based on commands received by the communication module from the primary IMD or external device. Other configurations will become apparent to those skilled in the art based on the foregoing.

It will further be appreciated that the systems and methods according to the various embodiments of the present invention are adaptable for use with both rechargeable and single-use IMDs.

Various modifications and additions can be made to the exemplary embodiments discussed without departing from the scope of the present invention. For example, while the embodiments described above refer to particular features, the scope of this invention also includes embodiments having different combinations of features and embodiments that do not include all of the described features. Accordingly, the scope of the present invention is intended to embrace all such alternatives, modifications, and variations as fall within the scope of the claims, together with all equivalents thereof.

We claim:

1. A method carried out by a satellite implantable medical device for being awakened from a sleep state by a primary implantable medical device, the satellite implantable medical device including a wake-up sensor, a control module, a physiologic sensor, a power supply, and a communication module, the method comprising:
   waiting in a sleep state, wherein only sensing circuitry of the wake-up sensor is energized and powered on for detecting and processing an output voltage from the wake-up sensor;
   detecting, by the wake-up sensor, the presence of an electromagnetic wake-up field generated by the primary implantable medical device;
   responsive to detecting the presence of the electromagnetic wake-up field, prompting power control circuitry coupled to the power supply to supply electrical power to the control module and the communication module, causing the control module and communication module to change from the sleep state to an active state; and
   wherein, in the active state, the control module causes the physiologic sensor to activate and sense at least one physiologic parameter, and the communication module to wirelessly transmit the at least one sensed physiologic parameter to the primary implantable medical device.

2. The method of claim 1 wherein the communication module is adapted for acoustic communication, and further wherein the physiologic sensor includes a pressure sensor adapted to measure pressure within a blood vessel, and wherein the at least one physiologic parameter is a pulmonary arterial blood pressure.

3. The method of claim 1 further comprising:
   inductively coupling a first inductive coil of the primary implantable medical device to a second inductive coil of the satellite implantable medical device; and
   passing an alternating current through the first inductive coil to generate an electromagnetic field,
   wherein the detecting step comprises detecting the electromagnetic field by the second inductive coil and generating an output voltage across the second inductive coil.

4. A method of waking an implantable medical device from a low-power state, the method comprising:
   providing a first implanted medical device including a wake-up field generator and a first communication module, the wake-up field generator adapted to generate an electromagnetic wake-up field;
   providing a second implanted medical device including a battery, a wake-up sensor operable to detect the electromagnetic wake-up field, a physiologic sensor, a control module, and a second communication module configured to acoustically communicate with the first implanted medical device, wherein the second implanted medical device is initially in a low-power state in which only sensing circuitry of the wake-up sensor is energized and powered on for detecting and processing an output voltage from the wake-up sensor;
   detecting, by the wake-up sensor, the presence of the electromagnetic wake-up field generated by the first implanted medical device;
   responsive to detecting the presence of the electromagnetic wake-up field, prompting power control circuitry coupled to the battery to supply electrical power to the control module and the communication module, causing the control module and the communication module to change from the low-power state to an active state; and
   wherein, in the active state, the control module causes the physiologic sensor to activate and sense at least one physiologic parameter, and the second communication module to acoustically transmit the at least one sensed physiologic parameter to the first implanted medical device.

5. The method of claim 4 wherein the physiologic sensor includes a pressure sensor, and wherein the at least one physiologic parameter is a pulmonary arterial blood pressure.

6. The method of claim 4 further comprising:
   inductively coupling a first inductive coil of the first implanted medical device to a second inductive coil of the second implanted device; and
   passing an alternating current through the first inductive coil to generate an electromagnetic field,
   wherein the detecting step comprises detecting the electromagnetic field by the second inductive coil and generating an output voltage across the second inductive coil.

7. A system for waking up an implantable medical device from a sleep state, the system comprising:
   a primary implantable device including a wake-up field generator operable to generate an electromagnetic wake-up field, and a first communication module; and
   a satellite implantable device including:
     a control module;
     a pressure sensor adapted to sense blood pressure within a body lumen;
     a second communication module configured to acoustically communicate with the first communication module, wherein the control module and the second communication module are adapted to change between a sleep state and an active state in response to the electromagnetic wake-up field; and
     means for detecting the electromagnetic wake-up field.

8. The system of claim 7 wherein the wake-up field generator includes a first inductive coil, and wherein the means for detecting the wake-up field include a second inductive coil inductively coupled to the first inductive coil.

9. The system of claim 7 wherein the satellite implantable device further comprises timer circuitry operable to cause, at a first predetermined time interval, the means for detecting the wake-up field adapted to change from a sleep state to an active state in which the means for detecting the wake-up field are operable to detect the wake-up field.

10. The system of claim 9 wherein the timer circuitry is further adapted to cause the means for detecting the wake-up field to return to the sleep state upon passage of second predetermined time interval.

11. The system of claim 10 wherein the wake-up field generator includes a magnetic field generator, and wherein the means for detecting the wake-up field include a magnetic field sensor.

12. The system of claim 10 wherein the wake-up field generator is adapted to generate a physiologically sub-threshold electrical excitation current, and wherein the means for detecting the wake-up field include an electric field sensor adapted to detect the excitation current.

* * * * *

UNITED STATES PATENT AND TRADEMARK OFFICE
CERTIFICATE OF CORRECTION

| | | |
|---|---|---|
| PATENT NO. | : 7,650,185 B2 | Page 1 of 1 |
| APPLICATION NO. | : 11/380112 | |
| DATED | : January 19, 2010 | |
| INVENTOR(S) | : Maile et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 866 days.

Signed and Sealed this

Twenty-third Day of November, 2010

David J. Kappos
*Director of the United States Patent and Trademark Office*